United States Patent [19]
Kalt et al.

[11] Patent Number: 5,308,339
[45] Date of Patent: * May 3, 1994

[54] UNIVERSAL CLAMP

[75] Inventors: Glenda G. Kalt, Boca Raton, Fla.; Dale K. Straub, Alhambra, Calif.; Peter Piwonka, Munich, Fed. Rep. of Germany

[73] Assignee: Medical Distributors, Inc., Boca Raton, Fla.

[*] Notice: The portion of the term of this patent subsequent to Jun. 13, 2006 has been disclaimed.

[21] Appl. No.: 956,829

[22] Filed: Oct. 5, 1992

Related U.S. Application Data

[60] Continuation of Ser. No. 740,911, Aug. 6, 1991, abandoned, which is a division of Ser. No. 366,300, Jun. 30, 1989, Pat. No. 5,037,397, and a continuation of Ser. No. 86,473, Aug. 16, 1987, Pat. No. 4,838,867, and a continuation-in-part of Ser. No. 28,927, Mar. 23, 1987, Pat. No. 4,838,878, which is a division of Ser. No. 730,344, May 3, 1985, Pat. No. 4,702,736, and a continuation-in-part of Ser. No. 813,730, Dec. 27, 1985, Pat. No. 4,738,662, which is a continuation-in-part of Ser. No. 730,344, Dec. 27, 1985.

[51] Int. Cl.⁵ .................................................. A61M 5/32
[52] U.S. Cl. ............................... 604/180; 128/DIG. 26
[58] Field of Search .................. 604/174, 179, 180; 128/DIG. 26

[56] References Cited

U.S. PATENT DOCUMENTS

| | | |
|---|---|---|
| 998,901 | 10/1976 | CAX . |
| 2,707,953 | 5/1955 | Ryan . |
| 2,735,432 | 2/1956 | Hudson . |
| 3,046,989 | 7/1962 | Hill . |
| 3,059,645 | 10/1962 | Hasbrouck et al. . |
| 3,161,199 | 12/1964 | Shaw (Sands) . |
| 3,288,136 | 11/1966 | Lund . |
| 3,324,853 | 6/1967 | Czorny et al. . |
| 3,358,141 | 12/1967 | Hoffmann et al. . |
| 3,630,195 | 12/1971 | Santomieri . |
| 3,696,920 | 10/1972 | Lahay . |
| 3,702,612 | 11/1972 | Schlesigner . |
| 3,713,448 | 1/1973 | Arrott . |
| 3,782,383 | 1/1974 | Thompson et al. . |
| 3,826,254 | 7/1974 | Mellor . |
| 3,834,380 | 9/1974 | Boyd . |
| 3,972,321 | 3/1976 | Proctor . |
| 4,018,221 | 4/1977 | Rennie . |
| 4,088,136 | 5/1978 | Hasslinger . |
| 4,142,527 | 3/1979 | Garcia . |
| 4,165,748 | 8/1979 | Johnson . |
| 4,221,215 | 9/1980 | Mandelbaum . |
| 4,275,721 | 6/1981 | Olson . |
| 4,329,984 | 5/1982 | Kervin . |
| 4,331,144 | 5/1982 | Wapner . |
| 4,416,664 | 11/1983 | Womack . |
| 4,417,710 | 11/1983 | Adair . |
| 4,531,942 | 3/1985 | Turner . |
| 4,534,762 | 8/1985 | Heyer . |
| 4,583,976 | 4/1986 | Ferguson . |
| 4,617,017 | 10/1986 | Hubbard et al. . |
| 4,669,458 | 6/1987 | Abraham et al. . |
| 4,678,462 | 7/1987 | Vaillancourt . |
| 4,699,616 | 10/1987 | Nowak et al. . |
| 4,702,736 | 10/1987 | Kalt et al. . |
| 4,738,662 | 4/1988 | Kalt et al. ............ 604/180 |
| 4,838,867 | 6/1989 | Kalt et al. ............ 604/180 |
| 4,838,878 | 6/1989 | Kalt et al. . |

References Cited
FOREIGN PATENT DOCUMENTS

CA 998,901 10/1976 Canada ..............................

Primary Examiner—Stephen G. Pellegrino
Assistant Examiner—Michael Rafa
Attorney, Agent, or Firm—Ruden, Barnett, McClosky, Smith, Schuster & Russell

[57] ABSTRACT

A clamp for holding an article to an object including a base means for adhering the clamp to the object, a flap, securing means for securing the flap to the base means with the article positioned therebetween and resilient pad means having an adhesive surface for contacting the article. The securing means includes a first holding means for holding a first portion of the flap and a second holding means for holding a second portion of the flap. Both holding means may be releasable. The second holding means is spaced from the first holding means a sufficient distance along the flap for the article to lie between them. Resilient adhesive surfaces are provided on the flap and base means for contacting and adhering the article.

8 Claims, 8 Drawing Sheets

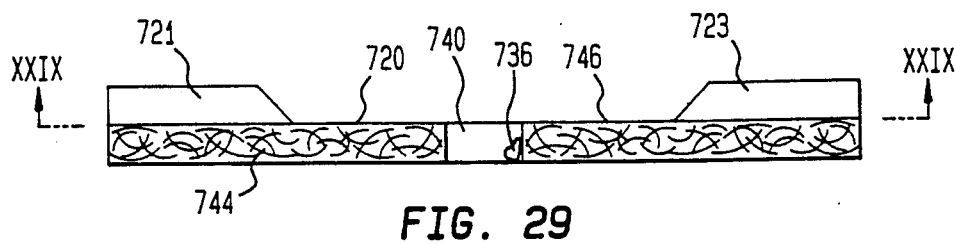
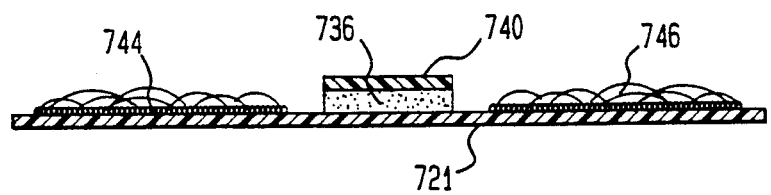
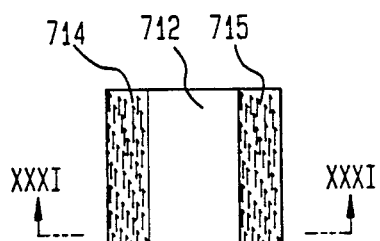
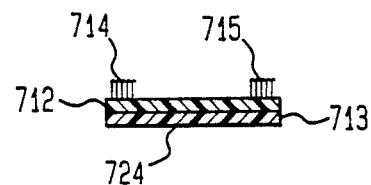
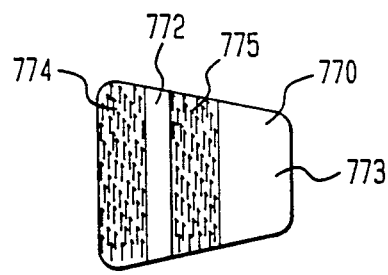
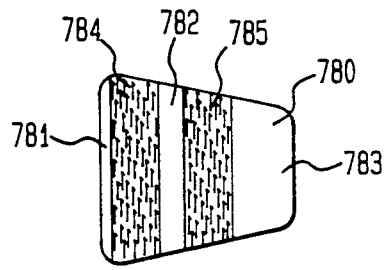
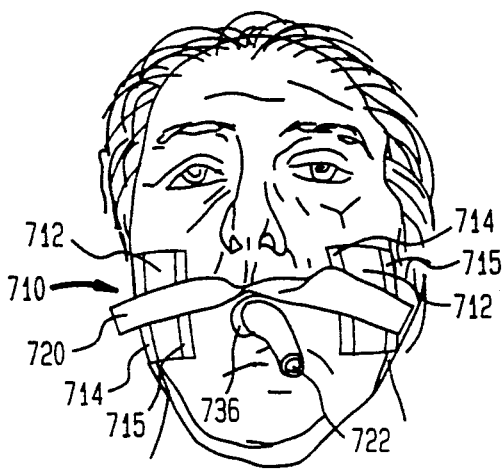

UNIVERSAL CLAMP

This is a continuation of application Ser. No. 740,911, filed Aug. 6, 1991, now abandoned, which is a divisional of application Ser. No. 366,300, filed Jun. 30, 1989 now U.S. Pat. No. 5,037,397; and a continuation of Ser. No. 086,473, filed Aug. 16, 1987 now U.S. Pat. No. 4,838,867; and a continuation-in-part of Ser. No. 028,927, filed Mar. 23, 1987 now U.S. Pat. No. 4,838,878 which is a division of Ser. No. 730,344, filed May 3, 1985 U.S. Pat. Nos. 4,838,878, 4,762,756 and a continuation-in-part of Ser. No. 813,730, filed Dec. 27, 1985 U.S. Pat. No. 4,738,662 which is continuation-in-part of Ser. No. 730,344, filed May 3, 1985 U.S. Pat. No. 4,702,736.

BACKGROUND OF THE INVENTION

The present invention relates in general to a clamp for holding an article and more particularly to a medical clamp for holding a tube to a patient's body.

It is often necessary to clamp external and mesentery tubes to a medical patient's body, for example, feeding tubes, nao-gastric tubes, chest tubes, foley catheter as well as condom catheter tubes, dialysis tubes, endotracheal tubes, angiocath and heparin lock set tubes, as well as other tubes used to introduce fluids into the body intravaneously or to introduce oxygen into the mouth or nose of a patient.

It is important that a tube clamp holds the tube firmly because movement of the tubes may cause discomfort to the patient. It is often necessary to remove the tube and replace it with another or to adjust the position of the tube. Therefore, it is desirable that the clamp be releasable so that the tube may be unclamped and reclamped without removing or replacing the entire clamp structure.

U.S. Pat. No. 3,826,254 discloses a clamp comprising an adhesive pad which folds back over itself to adhere a tube.

U.S. Pat. No. 4,165,748 discloses a tube clamp formed in one piece and adhered to a patient's body and having a center portion which folds around and clamps the tube by adhering to itself.

U.S. Pat. No. 4,333,468 discloses a clamp having a base having two raised portions to form between them a transverse groove. A tube is accepted to lie in the groove and a flap permanently affixed to the base at one end is extendable over the tube. Pressure sensitive adhesive covers the raised portions and the groove of the base as well as the flap underside. The flap is pressed onto the raised portions and the tube to adhere and clamp the tube in the groove.

Each of the foregoing clamps suffers the disadvantage that slight rotation or translation of the tube tends to break the adhesive bond. Thus secure holding of the tube is not effected.

U.S. Pat. No. 3,834,380 discloses a clamp including a slit tube which receives a rod-like article and is closed and kept closed by a flap attached to the tube at one end and secured at the other end. The tube is flexible and may be resilient. This device is unduly bulky and may cause discomfort to the patient and tends to lift the clamp tape off of the patient which causes further discomfort. However, this device is insufficiently flexible for use in areas of the body where movement is likely and flexibility is desired. Such areas include the head and joint areas. This inflexibility may result in a tube being held in a wrong position. Moreover, this device depends on friction for holding a tube, and is therefore dependent upon the surface properties of the article or tube to be held to effect such a friction bond. If the surface of the article to be held is "slippery" relative to the material of the slit tube, the holding effect will be poor. A further disadvantage of this device is that only a small range of sizes of tubes may be held for a given slit tube size.

Haerr, U.S. Pat. No. 4,122,857 discloses a substantially rectangular pad of soft, strong, flexible, foam material provided with a secure flap by which an article such as a catheter tube or the like may be anchored to the pad which in turn is adapted to be adhesively affixed to the skin of the patient.

Thomas, U.S. Pat. No. 3,677,250 discloses a mouth tube clamp that is not adjustable once it is positioned.

SUMMARY OF THE INVENTION

The present invention alleviates to a great extent the disadvantages of prior devices by providing a clamp for holding an article to an object including a base means for adhering the clamp to the object, a flap, securing means for securing a flap to the base means with the article positioned therebetween, and resilient pad means having an adhesive surface for contacting the article. In one aspect of the invention, the securing means includes a first holding means for holding a first portion of the flap and a second holding means for holding a second portion of the flap. The second holding means is spaced along the flap from the first holding means a sufficient distance for the article to lie between them. The resilient pad means is deformable such that slight rotational or translational movement will deform the pad rather than break the adhesive bond between the pad and the article.

It is an object of the present invention to provide a clamp for holding an article.

It is a further object of the present invention to provide a clamp having a resilient adhesive pad in contact with the held article to inhibit the breaking of the adhesive bond as a result of rotational or translational movement of the article.

It is another object of the invention to provide a medical clamp to releasably hold a tube to allow removal of the tube and repositioning of the tube without removal of the clamp from the patient's body.

It is yet another object of the invention to provide a medical clamp yielding the foregoing advantages and that effectively holds a tube against transverse and rotational movement.

It is still another object of the present invention to provide a medical clamp yielding the foregoing advantages and that is simply and economically constructed.

It is still a further object of the present invention to provide a medical clamp yielding the foregoing advantages and that can clamp a variety of sizes of tubes.

BRIEF DESCRIPTION OF THE DRAWINGS

FIG. 28 is a plan view of the flap of an eighth preferred embodiment of the present invention.

FIG. 29 is a view taken along section line XXIX—XXIX of FIG. 28.

FIG. 30 is a plan view of the base of the eighth preferred embodiment.

FIG. 31 is a view taken along section line XXXI—XXXI of FIG. 30.

FIG. 32 is a view of the eighth preferred embodiment in use.

FIG. 33 is a view like FIG. 31 showing an alternate base construction.

FIGS. 34 and 35 are views like FIG. 30 showing alternate base constructions.

DETAILED DESCRIPTION OF THE PREFERRED EMBODIMENTS

As referred to herein, the inner surfaces of various component parts of the preferred embodiments of the present invention are those surfaces oriented towards the object to which the clamp is adhered. Similarly, the outer surfaces of the various component parts of the preferred embodiment are those surfaces oriented away from such object. Such object may be any object but for medical clamps will most likely be the patient's skin, the patient's clothing, bandages, casts or the like.

Figure 1:
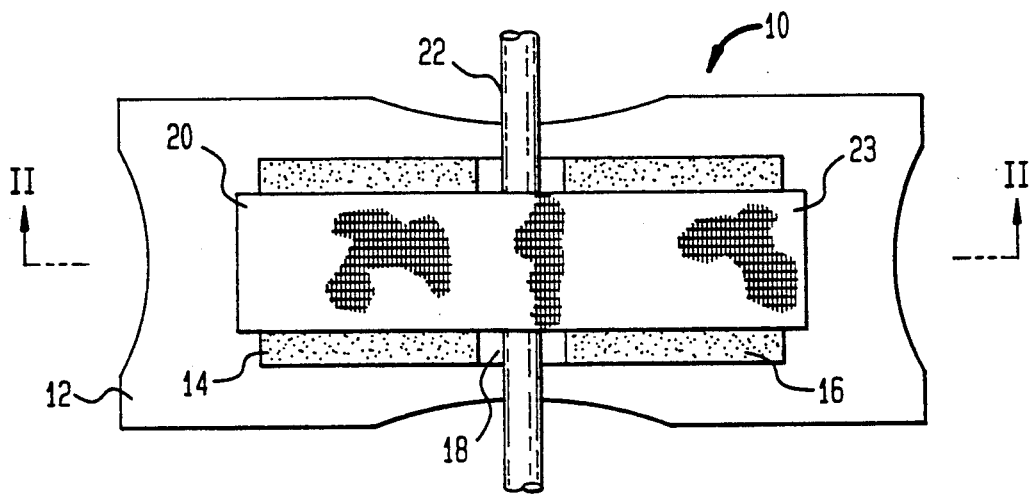
FIG. 1 is a plan view of a first embodiment of a medical clamp according to the present invention.
Figure 2:
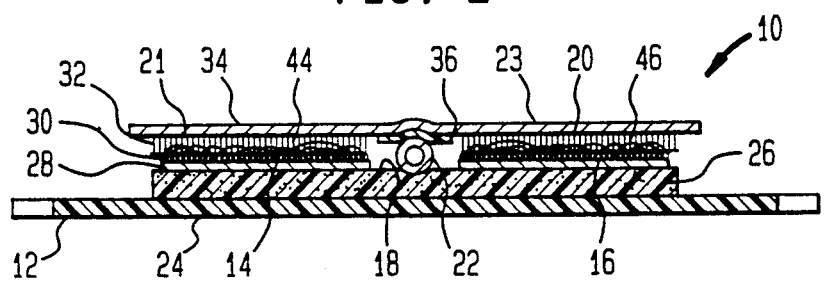
FIG. 2 is a view taken along section line II—II of FIG. 1.

Referring now to FIGS. 1 and 2 there is shown a medical clamp, generally designated by reference numeral 10, according to a first preferred embodiment of the present invention. In the first preferred embodiment, clamp 10 is particularly suitable for holding a tube 22 to the skin of a medical patient. The base means for adhering clamp 10 to the patient includes a base 12 that is preferably composed of medical grade tape such as 3M-1527L marketed by 3M Company under the registered trademark "Transpore". Base 12 is coated on its inner surface 24, with a medical grade adhesive, preferably a hypoallergenic synthetic acrylic pressure sensitive adhesive.

Flap 20 extends outside the tube 22 and is secured to base 12 by securing means to hold tube 22 therebetween. In the first preferred embodiment, securing means includes an adhesive pad 26 and hook and loop fastening material 32 and 30 as described in more detail below.

Flap 20 includes a hook base fabric 34 into which is woven fabric 32 of the securing means. In the preferred embodiment hook fabric 32 defines hook pads 44 and 46. Hook pad 44 is woven into a first portion 21 of flap 20 and hook pad 46 is woven into second portion 23 of flap 20. Hook fabric 32 is absent from region 38 of flap 20 between pads 44 and 46.

Adhesive pad 26 is positioned on the outer surface of base 12. Pad 26 is composed of a resilient material and is coated on both its outer and inner surfaces with a medical grade adhesive. Pad 26 is preferably a polyvinyl chloride foam such as 3M-1511 available from 3M Company. The thickness of pad 26 is preferably between five and two hundred mils and more preferably about thirty five mils.

First loop pad 14 and second loop pad 16 are composed of a loop material that includes loop fabric 30 and base fabric 28. Pads 14 and 16 are adhered at base fabric 28 by medical grade adhesive to the outer surface of pad 26. Loop pads 14 and 16 are adapted to mate with first hook pad 44 and second hook pad 46, which are woven to first portion 21 and second portion 23, respectively, of flap 20 to, with adhesive pad 26, secure flap 20 to base 12. The hook and loop materials are available from 3M Company under the registered trademark "Scotchmate".

In the first preferred embodiment, flap 20 may be constructed by removing hooks from stock hook material to form region 38. This may be accomplished by ultrasonic welding equipment and techniques. Alternatively, a separate flap material may be provided with individual hook pads, each including backing and hook fabric, adhered to the inner surface of such material in spaced relationship so as to form region 38.

In the first preferred embodiment the loop material has been provided to face outwards because loop material is typically softer than hook material and will not discomfort the patient if her skin should rub against it.

Tube 22 extends between pad 14 and pad 16 along the region 18 of pad 26. Hooks 32 are not present on flap 20 in region 38 in facing correspondence with region 18. Pad 36 which is similar in construction to resilient pad 26 and having adhesive inner and outer surfaces is adhered to the inner surface of flap 20 at region 38. Resilient pad 36 and region 18 of resilient pad 26 define the resilient pad means of the first preferred embodiment.

It has been found that the utilization of a resilient adhesive material such as 26 in contact with a tube provides a secure means for holding the tube against rotational or translational movement. This may be because in use the resilient material tends to deform and move with the tube when the tube is urged to rotate slightly or to translate slightly. Because the resilient material deforms, the bond of the adhesive with the tube is stressed to a lesser degree and is less likely to be broken. Significant deformation must occur before the resilient material will resist further deformation with such a force that the adhesive bond between the pad and the tube is broken. Accordingly, significant movement of the tube is possible prior to the breaking of the adhesive bond. Conversely, in prior clamps where no resilient adhesive pads are provided, any rotational or translational movement of the tube, with respect to the clamp adhesive surfaces, which movement may be caused by the bumping of the tube by the patient, may more likely result in the breaking of the adhesive bond holding the tube.

Figure 3:
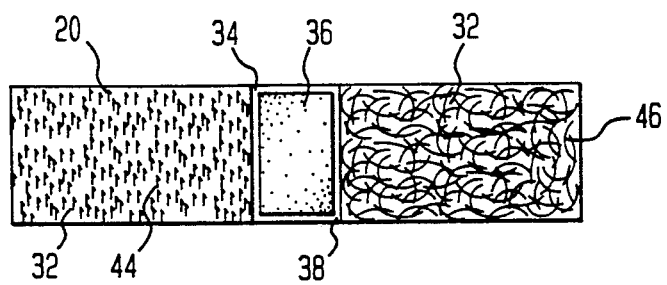
FIG. 3 is a view of the inner surface of flap 29 of FIG. 1.
Figure 4:
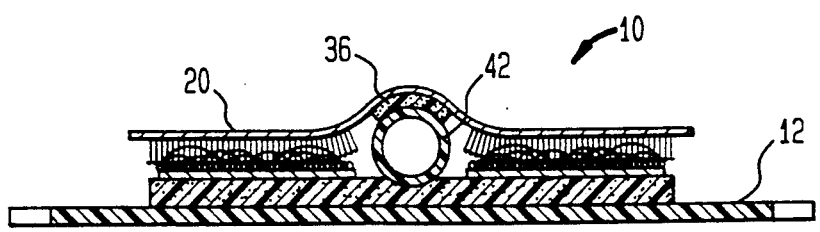
FIG. 4 is a view like FIG. 2 illustrating the clamping of a relatively larger tube.

FIG. 3 illustrates the inner surface of flap 20. FIG. 4 illustrates clamp 10 holding tube 42 which is larger in diameter than tube 22 of FIG. 1.

Figure 5:
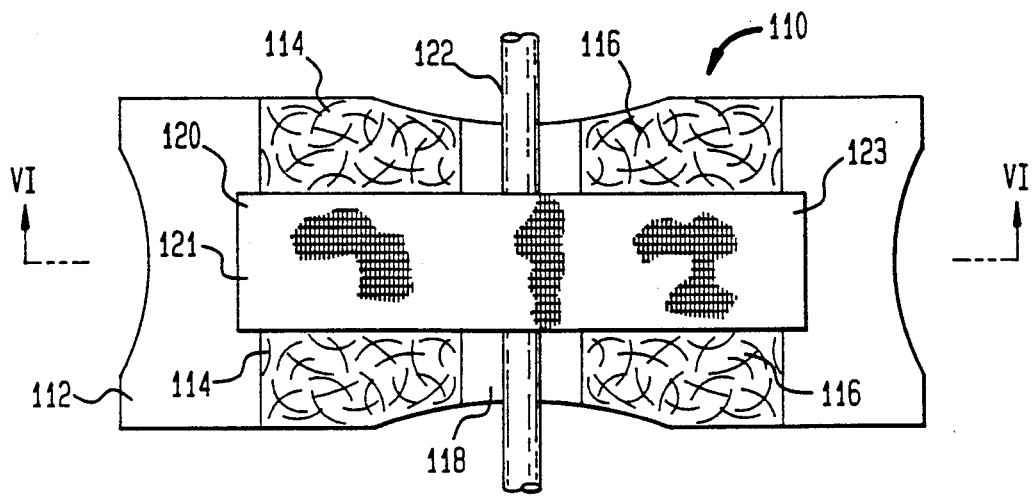
FIG. 5 is a plan view of a second embodiment of a medical clamp according to the present invention.
Figure 6:
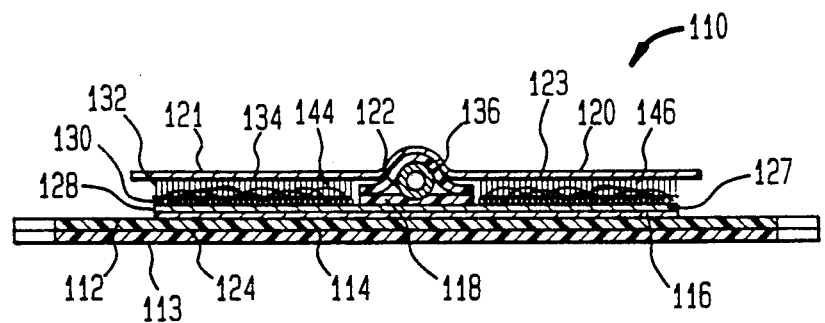
FIG. 6 is a view taken along section VI—VI of FIG. 5.
Figure 7:
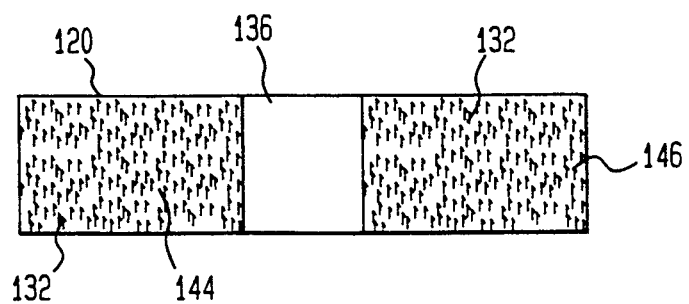
FIG. 7 is a view of the inner surface of flap 120 of FIG. 5.

Refer now to FIGS. 5 through 7 which illustrate a second preferred embodiment of the present invention. A clamp according to the second preferred embodiment of the invention, generally designated by reference numeral 110, is similar in construction to the first preferred embodiment described in conjunction with FIGS. 1 through 4, with the difference in the two embodiments residing primarily in the construction of the resilient pad means.

Clamp 110 includes base 112 that is preferably composed of medical grade tape similar to that described for the first preferred embodiment. Base 112 is coated on its inner surface 124 with a medical grade adhesive. Flap 120 extends outside of tube 122, the article to be held, and is secured to base 112 by securing means to hold tube 122 therebetween.

In the second preferred embodiment, the securing means includes a transfer tape 127 which has adhesive applied to both sides, the outer and inner sides, to function to hold loop fabric backing 128 to base 112. With reference to FIGS. 5 and 6, preferably transfer tape 127 underlies the whole area of loop fabric backing 128 to securely hold the loop backing fabric to base 112. Loop fabric backing 128 and loop fabric 130 woven thereto, extends through loop pad 114, resilient pad 118, and loop pad 116.

Resilient pad 118 is formed by applying a hot melt adhesive to the loop fabric 130 such that the applied adhesive extends up slightly above the top of the loops. When the hot melt adhesive cools and cures, it forms a resilient pad with an adhering outer surface. Medical grade hot melt adhesives suitable for this purpose include numbers DD5800, DD5900, DD5914 available from H. Fuller Adhesive Company. Preferably, the applied hot melt adhesive, when set up, or cured, will extend about one sixteenth of an inch above the loop material surface.

Flap 120 of the second preferred embodiment clamp 110, is made of hook fabric 132 woven into hook backing material 134. Similar to the loop material of the second preferred embodiment the hook material extends over the whole inside surface of flap 120 and the resilient pad 136 is formed by applying hot melt adhesive in the above-described fashion. Hook pad 144 to one side of hot melt adhesive resilient pad 136 is woven to a first portion of flap 120 and hook pad 146 to the other side of hot melt adhesive resilient pad 136 is woven to a second portion of flap 120. The first holding means for holding a first portion of flap 120 includes hook pad 144, loop pad 114, loop fabric backing 128, and transfer tape 127. The second holding means for holding a second portion of flap 120 includes hook pad 146, loop pad 146, loop fabric backing 128 and transfer tape 127. The first and second holding means function to releasably secure flap 120 to base 112.

Also illustrated in FIG. 6 is liner 113 which extends on the inner portion of base 112 to protect the adhesive surface thereof. When the clamp is to be used and to be adhered to an object such as the patient or piece of equipment or whatever, liner 113 is removed and fresh adhesive on surface 124 of base 112 is exposed.

Similarly, liners may be provided for covering the resilient adhesive pads 136 and 118 until those adhesive surfaces are to be utilized. This holds true for any of the embodiments herein, such liners may be provided where appropriate.

Figure 8:
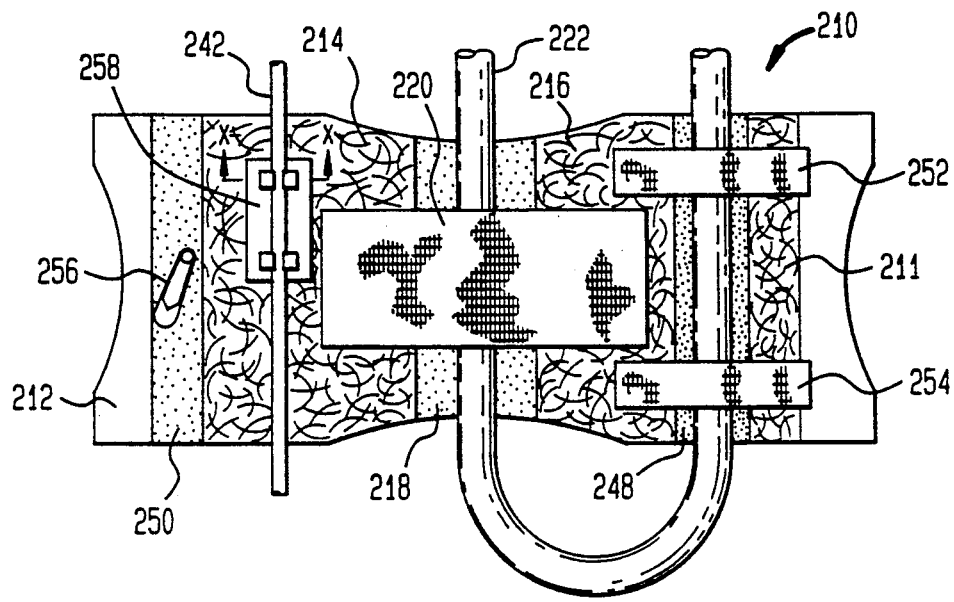
FIG. 8 is a plan view of a third embodiment of a medical clamp according to the present invention.
Figure 9:
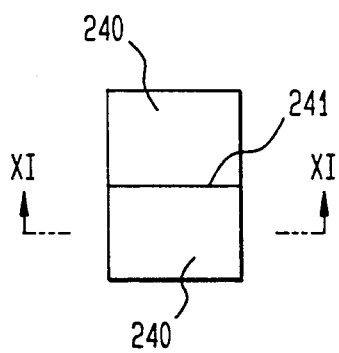
FIG. 9 is a plan view of a remote fastener used with the preferred embodiment of the present invention.
Figure 10:
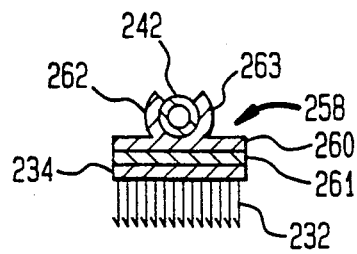
FIG. 10 is a view taken along section line X—X of FIG. 8.

Referring now to FIGS. 8 through 10, therein is illustrated a third preferred embodiment of the present invention. Clamp 210 illustrated therein, is similar in construction to either the first preferred embodiment or the second preferred embodiment, or a combination thereof, except that a plurality of adhesive pads are provided in parallel transverse arrangement.

Adhesive pad 250, adhesive pad 218 and adhesive pad 248 are provided as shown. Adhesive pads 218 and 248 each have loop material on either side. Loop pad 214 and loop pad 216 lie on either side of adhesive pad 218. Flap 220 extends across adhesive pad 218 and is secured to base 212 at both ends. Loop pad 216 and loop pad 211 are positioned on either side of adhesive pad 248. Note in this particular embodiment that tube 222 is clamped by flap 220 and turns and extends back again and is held to pad 248 by flaps 252 and 254.

Adhesive pad 250 does not have a loop pad on both sides. Pad 250 is useful for adhering objects to base 212 where a flap is not required. As shown, safety pin 256 is so adhered.

Another aspect of the present invention is illustrated by remote fastener 258 which is holding tube 242. Fastener 258 or others like it may be utilized to fasten instruments, blood pressure gauges, thermometers, tubes, "Y" joints, needles, wires, or whatever else may be required to be held out of the way in a hospital setting or other setting.

Referring to FIG. 10, there is shown a cross section of fastener 258. Fastener 258 includes base 260 having fingers 262 and 263 which extend and are angled towards one another to hold tube 242 therebetween. Base 260 is held to hook fabric backing 234 by transfer tape 261. Hook fabric 232 is woven into hook fabric backing 234.

Figure 11:
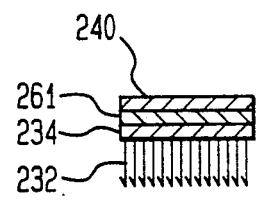
FIG. 11 is a view taken along section line XI—XI of FIG. 9.

A remote fastener 258 may come assembled as illustrated in FIG. 10, or alternatively may come as illustrated in FIGS. 11 and 9, with transfer tape 261 protected by liner 240. A slit 241 is provided in liner 240, and when the remote fastener is to be used, the liner 240 is removed and a base similar in construction to 260, or of some alternate construction adapted for a particular holding need, is attached to transfer tape 261 and thereby adhered to hook fabric and backing 232, 234. The remote fastener may now be attached to any available loop material to clamp the held article such as tube 242 to an object.

Yet another and fourth embodiment of the present invention is illustrated by FIGS. 12 through 15. The fourth preferred embodiment of a medical clamp, generally designated by reference numeral 310, is similar in construction to the embodiment of FIG. 1 except that flap 320 is held at its first portion 321 in a non-releasable manner.

Figure 12:
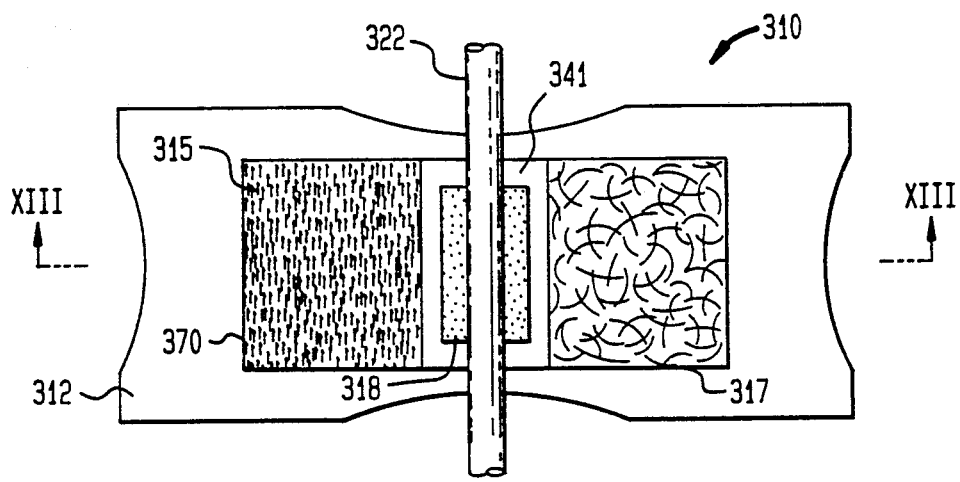
FIG. 12 is a plan view of a fourth preferred embodiment of the present invention showing the clamp open.
Figure 13:
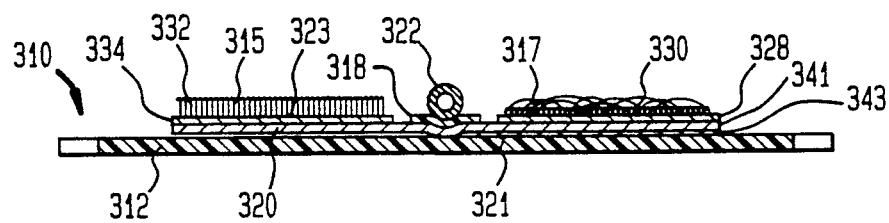
FIG. 13 is a view taken along section line XIII—XIII of FIG. 12.

Referring particularly to FIGS. 12 and 13, therein is shown a medical clamp according to the fourth preferred embodiment in its opened position. Flap 320 is composed of a substrate, preferably nylon, having a second portion hook fabric 332 woven to hook fabric backing 334 to form hook pad 315. Hook pad 315 is adhered to second portion 323 of flap 320. The nylon substrate that forms flap 320 extends past the first portion 321 of flap 320 and is adhered at the fixed portion 341 of the substrate to base 312 by transfer tape 343. Loop fabric 330 woven to loop fabric backing 328 is adhered to a fixed portion 341 of the substrate and forms loop pad 317. The area of substrate 341 which lies between hook pad 315 and loop pad 317 is provided with resilient pad 318. Tube 322 lies on resilient adhesive pad 318 in the open position of the fourth preferred embodiment as illustrated in FIGS. 12 and 13.

Figure 14:
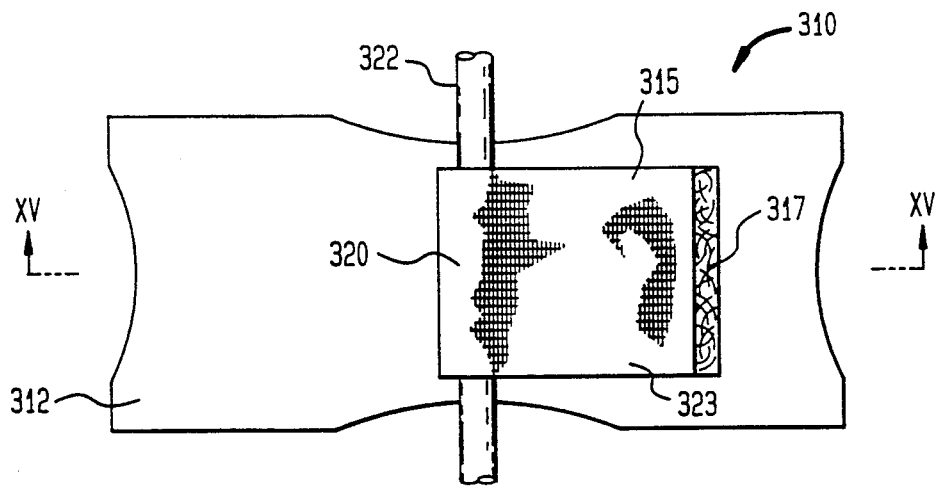
FIG. 14 is a view like FIG. 12 showing the clamp closed.
Figure 15:
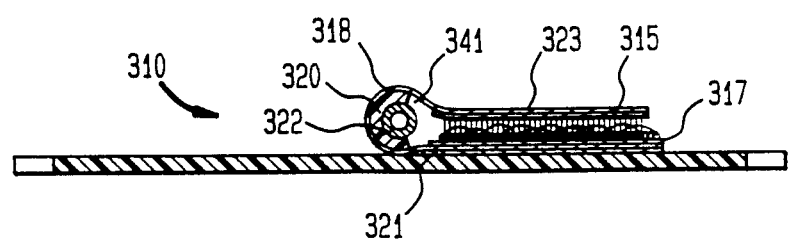
FIG. 15 is a view taken along section line XV—XV of FIG. 14.

Referring now to FIGS. 14 and 15, clamp 310 is shown in its closed position with flap 320 wrapped over tube 322 such that hook pad 315 mates with loop pad 317 to thereby hold the second portion 323 of flap 320 with transfer tape 321 and the affixed portion of substrate 341 to base 312. In the closed position resilient pad means, resilient pad 318 having an adhesive surface which contacts tube 322 functions to clamp tube 322 against rotation and translation.

Figure 16:
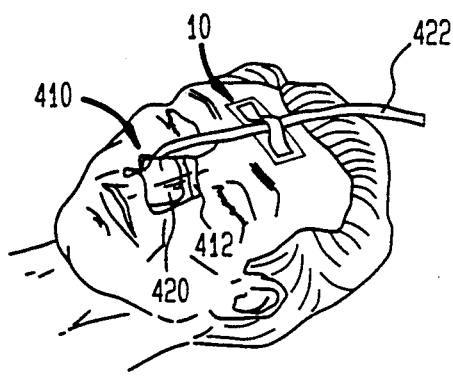
FIG. 16 is a perspective view of a fifth embodiment according to the present invention particularly suitable for clamping nasal tubes.

Refer now to FIG. 16 there being shown a perspective view of a tube clamp generally referred to by reference numeral 410 particularly suitable for clamping nasal tubes. As shown in FIG. 16, clamp 410 is in position on the nose of a patient to hold tube 422 in the patient's nasal passage. Clamp 14 includes a base portion 412 and a flap portion 420 described in greater detail with reference to FIGS. 17-19. Clamp 10 is similar to the clamp illustrated in FIG. 1 and may be utilized in conjunction with clamp 410 to secure tube 422 to the head of the patient in a manner which does not constrain his movements, particularly during sleep, and which minimizes the danger of the tube being torn from its position during normal movements when the patient is awake or asleep.

The preferred position for the tube in accordance with the foregoing is to, upon exiting the nasal passage, extend up along the bridge of the nose and across the forehead and top of the head. To accomplish this position the tube must be properly and securely held upon exiting the nose so that the tube may assume this position and direction yet not crimp so as to obstruct the flow of fluids therethrough. Clamp 410 is particularly adapted to hold the nasal tube in such a configuration without crimping.

Figure 17:
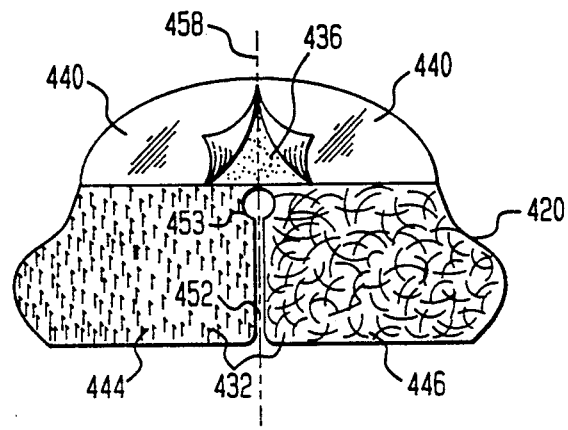
FIG. 17 is a plan view of the inner surface of the flap of the clamp of FIG. 16.
Figure 18:
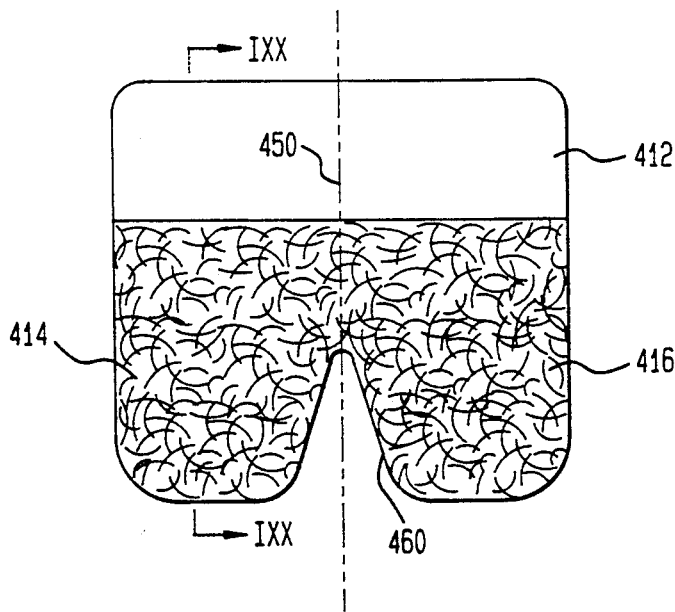
FIG. 18 is a plan view of the outer surface of the base of claim of FIG. 16.

Refer now to FIGS. 17 and 18 which illustrate base 412 and flap 420 of clamp 410. The inner surface of flap 420 is illustrated in FIG. 17. Flap 420 is generally symmetrical in the embodiment shown about axis line 458. Flap 420 is made of hook fabric and includes a first hook portion 444 and a second hook portion 446 on opposite sides of axis 458. Flap 420 has slit 452 which separates hook portions 444 and 446. Aperture 453 is provided at the inner end of slit 452 to enable easier spreading of hook portions 444 and 446 in use.

Flap 420 also includes a resilient adhesive pad 436 which lies generally symmetrically about axis 458 and through which slit 452 does not extend. Resilient pad 436 may be constructed in a similar fashion to the resilient pad means of the other embodiments illustrated herein. For example, resilient pad means 436 may be a hot melt adhesive applied to the appropriate area and allowed to dry and cure. Covering and protecting resilient pad means 436 is liner 440 which is shown in FIG. 17 in a partially removed position so that resilient pad means 436 may be viewed.

Refer now to FIG. 18 which illustrates the outer surface of base portion 412 of clamp 410. Base portion 412 is generally symmetric about axis line 450. Loop pads 414 and 416 lie on opposite sides of axis 450 and may be constructed of a single piece of loop fabric. As shown in FIG. 18, all of base 412 is not covered by loop fabric, however, alternatively the entire base portion could be so covered. Based 412 and the loop fabric forming pads 414 and 416 have a recess 460 formed therein generally symmetrically about axis 450. When the base 412 is applied to the patient's nose as shown in FIG. 16, recess 460 is preferably situated so that its innermost portion lies generally near the tip of the nose. The construction utilizing recess 460 allows the tube 422 to extend through the recess 460 while providing loop fabric material at a position lower down on the nose and cheek for attaching flap 420.

Figure 19:
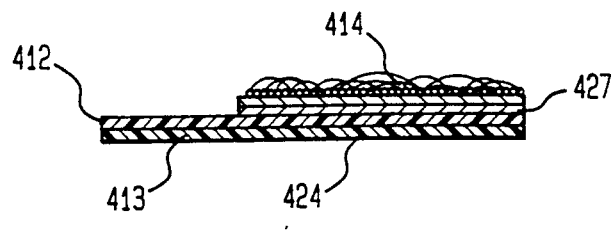
FIG. 19 is a view taken along section line IXX—IXX of FIG. 18.

Refer now to FIG. 19 which shows a section view of base 412. Based 412 has an adhesive inner surface 424 protected by removable liner 413. Loop pad 414 is adhered to base 412 by a layer of hot melted adhesive 427.

In use, clamp 410, liner 413 is removed and base 412 is positioned on the nose with the innermost portion of recess 460 proximate the tip of the nose. Then the tube is inserted into place in the nasal passage. Liner 440 is then removed from flap 420 to expose the adhering surface of resilient pad means 436. Pad 436 is wrapped around tube 422 with aperture 453 proximate the tip of the nose and axis line 458 positioned in general symmetry with the face and nose. The resilient pad means 436 may be pinched around the tube to adhere to the tube and to itself. Hook pad 444 and 446 are then pressed to loop pad 414 and 416 to secure flap 420 and tube 422 in position. In this manner, the tube is bent to an angle of about ninety degrees with the angle of the nostril without crimping the tube. As shown in FIG. 16, a second clamp 10 is used on the forehead to route the tube up along the bridge of the nose and across the top of the head.

Yet another and sixth embodiment of the present invention is illustrated by FIGS. 20 through 23. The sixth preferred embodiment of a medical clamp, generally designated by reference numeral 510, is similar in construction to the embodiment of FIGS. 12 through 15 except that flap 520 is composed of a fabric backing partially woven with hook fabric and partially woven with loop fabric.

Figure 20:
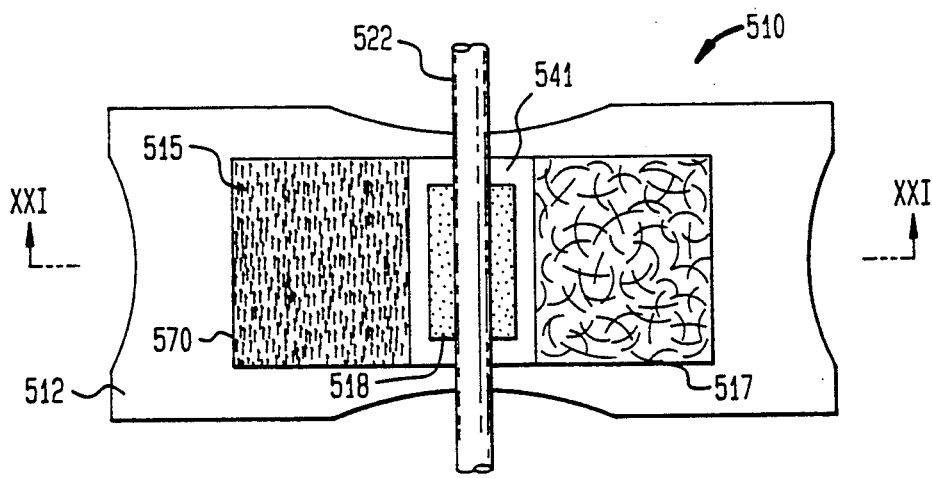
FIG. 20 is a plan view of a sixth preferred embodiment of the present invention showing the clamp open.
Figure 21:
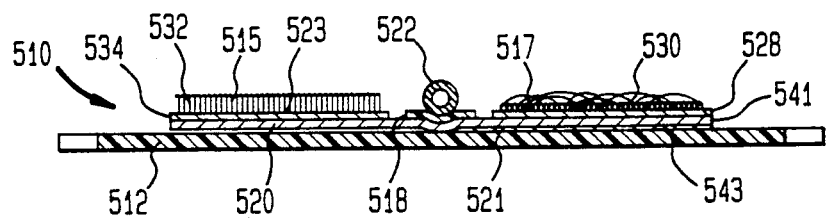
FIG. 21 is a view taken along section line XXI—XXI of FIG. 20.

Referring particularly to FIGS. 20 and 21, therein is shown a medical clamp according to the sixth preferred embodiment in its opened position. Flap 520 is composed of fabric backing, having a second portion 534 with hook fabric 532 woven thereto to form hook pad 515 which is thus adhered to second portion 523 of flap 520. The fabric backing that forms flap 520 extends past the first portion 521 of flap 520 and is adhered at the fixed portion of the fabric backing to base 512 by hot melt adhesive 543. Loop fabric 530 is woven to the fixed portion 541 of the fabric backing and forms loop pad 517. The area of fabric backing 541 which lies between hook pad 515 and loop pad 517 is provided with resilient pad 518 composed of hot melt adhesive. Although pad 518 only partially covers the area between pads 515 and 517, a complete covering or varying degrees of covering may be utilized as desired as long as tube 522 may be sufficiently clamped.

Figure 22:
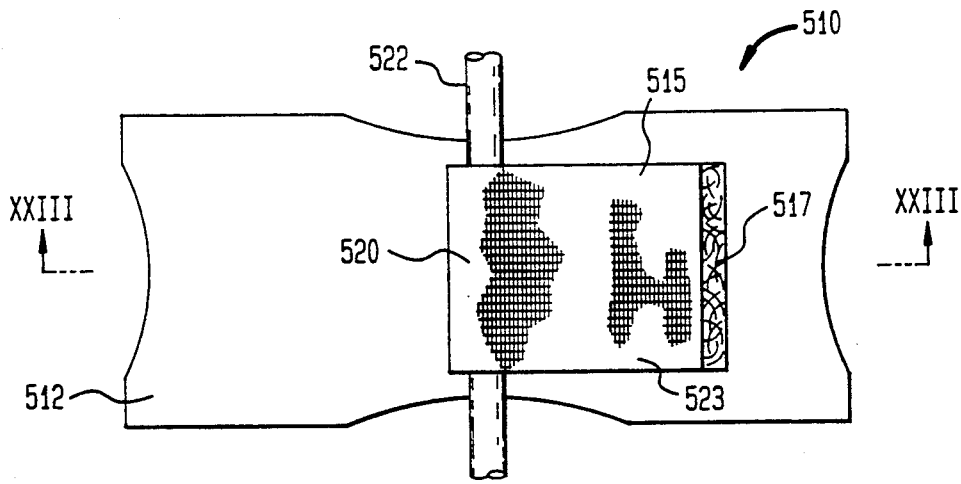
FIG. 22 is a view like FIG. 20 showing the clamp closed.
Figure 23:
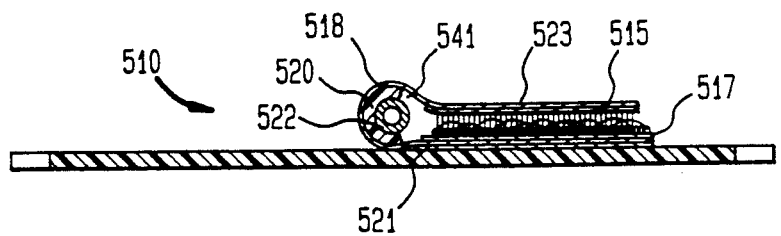
FIG. 23 is a view taken along section line XXIII—XXIII of FIG. 22.

Referring now to FIGS. 22 and 23, clamp 510 is shown in its closed position with flap 520 wrapper over tube 522 such that hook pad 515 mates with loop pad 517 to thereby hold the second portion 523 of flap 520 with hot melt adhesive 521 and the affixed portion of fabric backing substrate 341 to base 512. In the closed position resilient pad means, and resilient pad 518 having an adhesive surface which contacts tube 522, functions to clamp tube 522 against rotation and translation.

Figure 24:
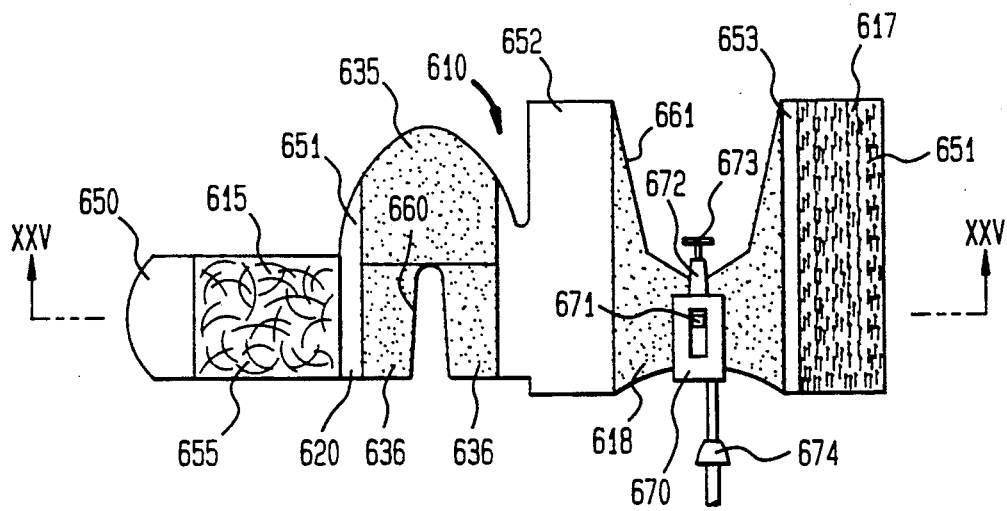
FIG. 24 is a plan view of a seventh preferred embodiment of the present invention showing the clamp opened.
Figure 25:
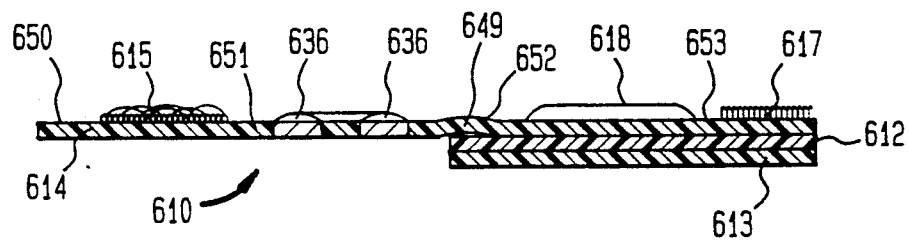
FIG. 25 is a view taken along line XXV of FIG. 24.
Figure 27:
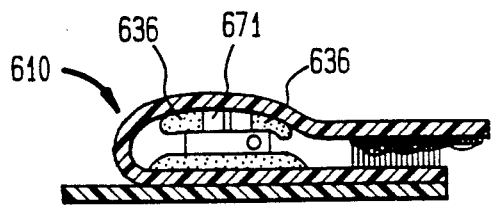
FIG. 27 is a view taken along section line XXVII—XXVII of FIG. 26.

Refer now to FIGS. 24 and 27 there being shown an embodiment of the present invention, generally designated by reference numeral 610, particularly adapted for use with so called hepburn type locks for catheter needles. These locks are used when an intravenous needles is left in place over an extended time and provides a coupling for removably attaching various other needles and/or tubes 674 for supplying medication, nourishment and the like. These locks generally require access to locking mechanisms for operating the devices between open and closed positions. In some types of these locks, after the IV needle has established communication with the vein, a flexible, plastic tube is inserted over the needle and into the vein and the needle is withdrawn. Thus the tube rather than the needle is left to establish fluid communication with the vein.

Figure 26:
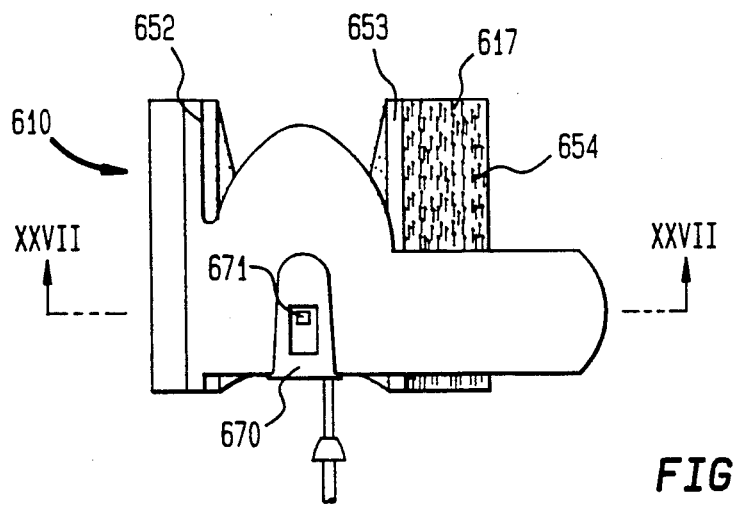
FIG. 26 is a view like FIG. 24 showing the clamp closed.

Clamp 610 includes a one piece substrate 649 having a medical grade double sided adhesive base 612 adhered to a portion thereof with a liner 613 which is removable for attaching the clamp 610 to the patient via base 612. Substrate 614 has hook material 617 woven into it in area 654 and loop material 615 woven to it at area 655. An absorbent pad 635 is positioned for soaking up blood and other fluids that may be present because of the puncture 673 caused by the IV needle 672. Slot 661 extends into the area of inner adhesive pad 618 so that the clamp 610 may be placed so that puncture 673 may be overlaid by absorbent pad 635. Resilient adhesive pad 636, made of a hot melt adhesive, lies adjacent absorbent pad 635. Slot 660 separates portions of adhesive pad 636 to allow access to the actuator 671 of the heperin lock IV 670 as shown in FIGS. 26 and 27. Resilient adhesive pad 618, also composed of hot melt adhesive, is also present for holding the IV 670. Note that pad 618 extends up to the sides of the puncture area with the clamp in place and when flap 620 of clamp 610 is folded over as shown in FIGS. 26 and 27 adhesive pad 618 contacts and holds absorbent pad 635.

Vacant regions 650, 651, 652 and 653 lie between the balance of the regions of the clamp discussed.

Referring now to FIG. 27 wherein the clamp is shown in use, note that pads 636 grasp the sides of the IV 670. Also note that loop material 615 engages hook material 617 for holding the clamp shut. As in prior embodiments the resilient pad 636 and 618 function to allow some movement of the IV 670 relative to the clamp through the twisting motion of the pad through its thickness. This results in increased comfort to the patient.

Refer now to FIGS. 28 through 33, there being shown a tube clamp, generally referred to by reference numeral 710, particularly suitable for holding an endotracheal tube. Clamp 710 may be used to hold other articles such as a foley catheter tube. In FIG. 32, clamp 710 is shown in position on the face of a patient to hold tube 722 in the patient's mouth and trachea. Clamp 710 includes two bases 712 and a flap 720.

The inner surface of flap 720 is illustrated in FIG. 28. Flap 720 is an elongated strip of loop fabric and includes a first loop portion 744 and a second loop portion 746. Flap 720 also includes a resilient adhesive pad 736 which lies between loop portions 744 and 746. Resilient pad 736 may be constructed in a similar fashion to the resilient pad means of the other embodiments illustrated herein. For example, resilient pad 736 may be a hot melt adhesive applied to the appropriate area of the flap and allowed to dry and cure.

In the illustrated embodiment, flap 720 is a single length of substrate material into which is sewn the loop portions 744 and 746 leaving a space of unsewn area between them when pad 736 is positioned. Other constructions, as discussed above, may include a continuous loop fabric with the hot-melt adhesive resilient pad applied directly on the loop fabric. Covering and protecting resilient pad 736 is liner 740 which is shown in FIG. 28 in a partially removed position so that resilient pad means 736 may be viewed.

Flap 720 includes finger hold portions 721 and 723 where the flap is wider than the loop material 744 and 746. Alternatively, the flap could be wider than the loop material along the entire length of the flap.

Refer now to FIG. 30 which illustrates the outer surface of base portion 712 of the clamp 710. The clamp 710 includes two base portions 712, one being positioned on each cheek. Base portion 712 is rectangular and includes two thin strips 714 and 715 of sewn-in hooks at its long peripheries. The minimum acceptable total area or the rectangular base portion is generally limited by the holding power of the adhesive to the race. This is a particularly relevant consideration because endotracheal tube holders are often used in emergency field situations where the skin may be damp or contaminated. To ensure strong holding of the flap to the base, the "mushroom" type hook and loop material may be used. It is available from Aplix Inc., U.S.A. of Charlotte, N.C. under catalog number MX20L000 for the loop in ⅝ inch width and MX16M000 for the hook in ⅝ inch width.

The rectangular base portion 712 is particularly advantageous from a manufacturing perspective because it may be made in a continuous strip with the hooks sewn in the edges. Hook pads 714 and 715 lie on opposite sides of base 712 which may be constructed of a single piece of substrate with hooks woven in only at portions 714 and 715. Additionally, the two strips increase versatility and holding force while decreasing the area of hook over the required base area and thus decreasing the cost.

The flap ends may be attached at any location along the base edges 714 and 715 and may be attached across one or both. Moreover, if the bases are turned such that the edges 714 and 715 point towards the mouth, the flap portions 744 and 746 may be secured along part or all of the length of one edge hook portions 714 and 715. The width of portions 744 and 746 are preferably wider than the width of edge portions 714 and 715 so that the entire width of the portion 714 and 715 may be engaged by the flap loop portion.

Refer now to FIG. 31 which shows a section view of the base 712. The base 712 is a continuous substrate and has an adhesive inner surface 724 protected by a removable liner 713. Hooks are sewn directly into the base 712. The base 712a of FIG. 33 is an alternate construction and includes separate hook strips 714a and 715a adhered at the edges of base 712a. Each base 712 and 712a may be formed in a continuous strip and cut to length.

In use of clamp 710, liner 713 is removed from two bases 712 which are positioned on the patient's cheek, preferably with the hook strips oriented to point towards the top of the head. Then the tube is inserted into place in the mouth and trachea. Liner 740 is then removed from flap 720 to expose the adhering surface or resilient pad 736. The pad 736 is wrapped around tube 722 just outside the mouth. The loop pads 744 and 746 are then pressed onto the hook pads 714, 715 to secure the flap 720 and tube 722 in position.

Refer now to FIGS. 34 and 35 which show alternate constructions for the bases. Bases 770 and 780 are tapered to contour to some extent with the patient's face, particularly when applied with the narrow portions 773, 783 pointing towards the ear. Regarding base 770, hook material strips 774 and 775 are separated by a vacant area 772. Area 773 is also vacant. This construction provides adequate surface area for adhering to the skin as discussed above and reduces the area of hook material while effectively holding at the periphery of base 770 by strip 774. Base 780 is similarly constructed with hook strips 784 and 785 separated by vacant area 782 and with vacant area 783. Strip 784 effectively holds at the periphery of base 780 being slightly set back by vacant strip 781.

The versitility of the construction enables repeated attachment, and adjustment of the flap to allow adjustment of the tube position and to hold a different size tube or tubes and air passageways that may be used with the tubes, without removing the cheek pads. The flap which is preferably a nonstretchable material is held firmly to the cheeks while the resilient adhesive pad allows some rotation and translation of the held tube.

In the preferred embodiments of the invention, medical grade adhesive and a hook and loop material is provided to secure flap 20 to base 12, however the present invention is not limited thereto, and other securing means may be used. For example hook material may be used in conjunction with a foam and fabric material. This is sometimes preferable if a somewhat lower holding force is required between the flap and the base. Moreover the fabric and foam material may be more breathable than a plastic base material and allow greater air transfer through the clamp to the patient's skin when used thereon.

Also, the clamp as described in the preferred embodiments are shown in a hospital setting, although as already pointed out, the clamps may be used in other settings, medical, medical related and non-medical, for holding articles to objects. For example, one such contemplated setting is in the electronics industry wherein the clamps may be used to secure wires within, around or between equipment. Another application is dentistry where the clamps may be used, for example, to hold tubes in the mouth.

What is new and desired to be protected by Letters Patent of the United States is:

1. A clamp for holding a nasal tube in a patient's nostril, said clamp comprising:
    a) a base for adhering said clamp to the patient's nose;
    b) a flap;
    c) a first securing device for releasably securing said flap to said base; and
    d) a second securing device for securing the nasal tube at an angle from the nostril without crimping the tube.

2. A clamp for holding an article to a patient, said clamp comprising:
    a) base means for adhering said clamp to the patient;
    b) flap means for engaging the article, said flap means having first and second ends and being formed separately from said base means; and
    c) securing means comprising a first holding means for releasably holding said first end of said flap means to said base means and a second holding means for holding said second end of said flap means to said base means, said second holding means being spaced from said first holding means a sufficient distance for the article to extend between said first and second holding means; and
    wherein said base means is shaped to be positionable simultaneously on both cheeks of the patient with said first holding means proximate to one cheek and said second holding means proximate to the other cheek.

3. A clamp as in claim 2, wherein said base means includes a first base portion and a second base portion, said first and second base portions being separately formed and independently attachable to either cheek.

4. A clamp as in claim 3, further comprising an outer resilient pad adhered to said flap between said first and second portions and having an adhesive surface for contacting the article.

5. A clamp as in claim 4, wherein said resilient pad includes a hot melt adhesive material.

6. A clamp as in claim 4, wherein said resilient pad includes loop material and hot melt adhesive material dispersed at least partially therethrough, said hot melt adhesive material extending over said loop material to form an adhesive surface covering over a portion of the loop material.

7. A clamp as in claim 6, wherein said resilient pad has a flap surface affixed to said flap, said flap surface being generally parallel to said adhesive surface to define the thickness of said resilient pad therebetween, said resilient pad being deformed through its thickness upon movement of the article adhesively bonded to said adhesive surface thereof relative to said flap such that said adhesive surface moves to a greater extent than said flap surface.

8. A clamp as in claim 7, wherein said adhesive surface is sized to accommodate and hold an endotracheal tube in position relative to the air passageway of a patient.

* * * * *